United States Patent [19]

Schwager et al.

[11] 3,981,925
[45] Sept. 21, 1976

[54] SELECTIVE HYDROFORMYLATION PROCESS USING HOMOGENEOUS CATALYSTS
[75] Inventors: Irving Schwager, Lompoc, Calif.; John F. Knifton, Poughquag, N.Y.
[73] Assignee: Texaco Inc., New York, N.Y.
[22] Filed: May 8, 1972
[21] Appl. No.: 251,639

[52] U.S. Cl. .......................................... 260/604 HF
[51] Int. Cl.² ........................................ C07C 45/08
[58] Field of Search .................. 260/604 HF, 617 R

[56] References Cited
FOREIGN PATENTS OR APPLICATIONS
1,138,601   1/1969   United Kingdom .......... 260/604 HF OTHER PUBLICATIONS
Bailar et al., Journ. of the Amer. Chem. Soc., vol. 89, pp. 1592–1599, Mar., 1967.

Primary Examiner—James O. Thomas, Jr.
Assistant Examiner—W. B. Lone
Attorney, Agent, or Firm—T. H. Whaley; C. G. Ries; Bernard Marlowe

[57] ABSTRACT

This invention relates to the hydroformylation of alkyl olefins to form aldehydes by the addition of hydrogen and carbon monoxide using ligand stabilized platinum-(II) dihalide complexes in combination with Group IVB metal halides as catalysts.

11 Claims, No Drawings

SELECTIVE HYDROFORMYLATION PROCESS USING HOMOGENEOUS CATALYSTS

SUMMARY OF INVENTION

This invention relates to the addition of hydrogen and carbon monoxide to olefins to obtain carbonyl containing compounds using improved ligand stabilized platinum(II) dihalide complexes with Group IVA metal halides.

More specifically, this invention concerns the hydroformylation of olefins, particularly alpha-olefins by the addition of hydrogen and carbon monoxide, under relatively mild reaction conditions using as catalysts ligand stabilized platinum(II) dihalides complexed with Group IVB metal halides.

BACKGROUND OF THE INVENTION

Aldehydes, particularly linear paraffinic aldehydes, are extremely useful as intermediates in organic synthesis because of their terminal carbonyl group which is among the most active groupings in organic compounds. For instance, they are easily reduced and oxidized and take part in a number of addition reactions. More specifically, paraffinic aldehydes are readily catalytically reduced to the primary alcohols, and oxidized to the corresponding carboxylic acids. They also undergo addition and/or condensation reactions with hydrogen cyanide, alcohols, nitroparaffins as well as condensations with themselves and other carbonyl-containing compounds. Further, these aldehydes condense with ammonia and its derivatives including primary amines. The latter condensation products (which are commonly known as Schiff's bases) lend themselves to applications as surfactants or detergents when solubilized by processes such as sulfation or oxyalkylation.

Generally, aldehydes as a class are produced commercially by the catalytic addition of carbon monoxide and hydrogen to olefins in an outgrowth of the well known Fischer-Tropsch process. This procedure is known as the "oxo" process, or more accurately as hydroformylation. The generic reaction is set forth below for an α-olefin:

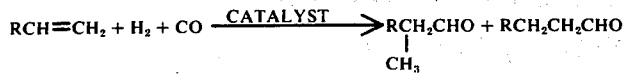

After an extensive research program the applicants have developed catalysts composed of ligand stabilized platinum(II) dihalide complexes with Group IVA metal halides that have several advantages over the known prior art. They include:

1. These catalysts permit successful operation of the hydroformylation process under relatively mild reaction parameters of temperature and pressure.
2. With these catalysts high olefin to catalyst ratios can be used without adversely affecting the advantages of the process.
3. These catalysts afford high yields of aldehydes, and selectivity to the more desirable straight chain aldehyde is high when α-olefins are hydroformylated.
4. Ordinary commercially available equipment may be used for the hydroformylation, and the use of relatively toxic cobalt or nickel carbonyls is avoided.

In view of this unusual combination of advantages, the inventive process represents an improvement in substance in view of the art.

In the broadest contemplated practice of this invention, aldehydes are produced in a catalytically directed addition of hydrogen and carbon monoxide to olefins by contacting at least a catalytic quantity of a ligand stabilized platinum(II) dihalide complex and a Group IVB metal halide catalyst at superatmospheric conditions of pressure, with said hydrogen, carbon monoxide and olefin until the desired formation of said aldehydes takes place.

In a preferred specific embodiment of the abovedescribed process essentially linear alkyl aldehyde products containing from 3 to 31 carbon atoms are prepared by the catalytic addition of hydrogen and carbon monoxide to alpha olefins containing 2 to 30 carbon atoms by the process steps comprising:

a. admixing each mole of said alpha-olefin to be hydroformylated in a deoxygenated reaction media with from 0.001 to 0.1 moles of a ligand stabilized platinum-(II) dihalide complex and from 0.001 to 1.0 moles of a group IVA metal halide, said mole ratio of Group IVA metal halide: ligand stabilized platinum(II) dihalide complex ranging from 1/1 to 10/1, b. pressurizing said reaction mixture to at least 100 psig with at least sufficient carbon monoxide and hydrogen to satisfy the stoichiometry of the hydroformylation reaction referred to supra, said mole ratio of $H_2:CO$ ranging from 30:1 to 1:30 moles of hydrogen for each mole of carbon monoxide;

c. heating said pressurized reaction mixture to temperatures between 25° to 125°C, until substantial formation of the predominantly linear alkyl aldehyde product is formed, and d. isolating said aldehyde products contained therein.

In still a further, preferred specific embodiment of the instant hydroformylation process, essentially linear alkyl aldehyde products containing from 3 to 31 carbon atoms are prepared from the catalytic addition of hydrogen and carbon monoxide to alpha-olefins containing 2 to 30 carbon atoms by the process steps comprising:

a. admixing under a deoxygenating reaction environment each mole of said alpha-olefin to be hydroformylated with a catalyst consisting of from 0.002 to 0.01 moles of a ligand stabilized platinum(II) dihalide complex and from 0.004 to 0.08 moles of a Group IVA metal halide, said mole ratio of Group IVA metal halide:ligand stabilized platinum(II) dihalide complex ranging from 2/1 to 8/1, b. pressurizing said reaction mixture to superatmospheric pressures ranging from 500 to 1500 psig with at least sufficient carbon monoxide to satisfy the stoichiometry of said hydroformylation reaction, and excess hydrogen over what is required to satisfy the stoichiometry of said hydroformylation reaction, said mole ratio of $H_2:CO$ ranging from 2/1 to 1/2 moles of hydrogen for each mole of carbon monoxide;

c. heating said pressurized reaction mixture to temperatures ranging between 50° and 100°C for a period of 1 to 30 hours to form the predominantly linear alkyl aldehyde product, and d. isolating said product contained therein.

In order to further aid in the understanding of this invention, the following additional disclosure is submitted:

A. PROCESS SEQUENCE AND VARIATIONS

In general, the components of the hydroformylation reaction mixture, including optional inert solvent, olefin and catalyst may be added in any sequence as long as good agitation is employed to provide a good dispersion or a homogeneous reaction mixture. For example, the following represent some variations insofar as the addition of catalyst components, inert solvents and olefin addition that may be made without departing from the inventive process. These modifications include:

1. The catalyst may be preformed and added preformed to the reaction solvent prior to the addition of the olefin and other inert solvent components.

2. Preferably, to minimize stability problems with the catalyst, the catalyst is best formed in situ usually by mixing the deoxygenated inert solvent and neat olefin, followed by the addition of the excess metal halide of Group IVA, and finally by the addition of the ligand stabilized platinum(II) complex to form the reaction mixture.

3. After using either variation 1 or 2, the deoxygenated catalyst containing reaction mixture is pressurized with CO and hydrogen and heated until the aldehyde product is formed.

4. An especially preferred modification, which minimizes both the induction period and the isomerization of the olefin, is the following: the catalyst is formed in a deoxygenated solvent; the catalyst solution is pressurized with carbon monoxide and hydrogen and heated to the desired reaction temperature; olefin is then added neat or dissolved in a suitable solvent. The reaction mixture is agitated under CO and $H_2$ at the desired reaction temperature until the aldehyde product is formed.

B. LIGAND STABILIZED PLATINUM(II)) TYPE - GROUP IVB METAL HALIDE CATALYST COMPLEX

The ligand-stabilized, platinum(II) type halide Group IVB metal halide complexes are known in the literature and methods for their preparation have been described.* One convenient mode of preparation in situ is to mix a solution of platinum(II) halide complex such as $PtCl_2[P(C_6H_5)_3]_2$, with a large molar excess of Group IVA metal halide, preferentially $SnCl_2$. While no structural configuration is advocated, nor is the success of the catalyst postulated upon a given structure, it is assumed that such a typical ligand-stabilized platinum-(II) typestannous chloride complex can be represented as:

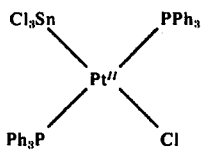

wherein Ph is the symbol for the phenyl radical ($C_6H_5$).

*For example: R. D. Cramer et al. J. A. Chem. Soc., 85, 1691(1963)

The ligand stabilized platinum(II) halide catalyst is only effective in the presence of a Group IVA metal halide as is shown in Table I. Illustrative of the Group IVA metal halides, which can be utilized with the ligand stabilized platinum(II) halide complexes to form active hydroformylation catalysts are: tin(II) chloride, tin(II) bromide, tin(II) iodide, tin(IV) chloride, germanium(II) chloride. Tables I and II show evidence of the suitability of these Groups IVA metal halides.

The platinum(II) halide complex, which is utilized in the presence of a Group IVA metal halide, should contain additional ligands with donor atoms from Groups VA, VIA and VIIA of the "Periodic Chart of Elements" (taken from the text "Advanced Inorganic Ghemistry" by F. A. Cotton and G. Wilkinson, 2nd Edition, John Wiley and Sons, New York, 1966), and have the general formula:

$$Ptx_2(LIGAND)_m$$

wherein x is a halogen, and m is an integer 2 or 1 depending upon whether the said ligand is monodentate or bidentate.

One class of ligands containing Group VA donor atoms, preferably trivalent phosphorus or arsenic, may be defined by the general formula:

wherein B represents the element from Group VA, preferably phosphorous or arsenic, R represents hydrogen atoms, aryl, alkyl, or aralkyl groups, which may contain less than 20 carbon atoms and need not be the same, A may represent oxygen, nitrogen or sulfur, or mixtures thereof, a has a value of 0 to 3, b has a value 3-a and c is equal to 1 or 2. It is also suitable for the organic radical R to contain functional groups, or to satisfy more than one of the valences of the Group VA atom, thereby forming a heterocyclic compound with the Group VA atom.

Another type of suitable ligand, containing Group VA donor atoms, is one which is comprised of two such Group VA atoms linked by organic radicals. This type of compound is called a bidentate ligand.

Another suitable class of Group VA ligands may be characterized by the formula:

wherein X may be an atom from Group VIIA, preferably chlorine and bromine, B represents a Group VA donor atom, preferably phosphorus and arsenic, R is an alkyl, aryl or aralkyl group which may contain less than 20 carbon atoms, and the sum of the integers $a$ plus $b$ is 3.

Another suitable class of ligands containing Group VA donor atoms consists of certain types of heteroaromatic ligands which may function as $\pi$-acceptor ligands.*

*For a description of $\pi$-acceptor ligands see Advanced Inorganic Chemistry by F. A. Cotton & G. Wilkinson, 2nd Ed. Chap. 27

Illustrative of suitable Group VA ligands which may be used with platinum(II) halides to form active hydroformylation catalysts in the presence of suitable Group IVA metal halides are:

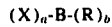

-continued

| | | |
|---|---|---|
| $P(CH_3)_2(C_6H_5)$, | $As(C_6H_5)_3$, | $As(n-C_4H_9)_3$, |
| $Sb(C_6H_5)_3$, | $Sb(n-C_4H_9)_3$, | $Bi(C_6H_5)_3$, |
| $Bi(n-C_4H_9)_3$, | $P(OC_6H_5)_3$, | $P(C_6H_{11})_3$, |
| $(C_6H_5)_2P-CH_2-CH_2-P-(C_6H_5)_2$, | $(C_6H_5)_2As-CH_2-CH_2As(C_6H_5)_2$, | |
| $P(Cl)(C_6H_5)_2$, | $P(Br)(C_6H_5)_2$, | $As(Cl)(C_6H_5)_2$, |
| $P(CH_3)(C_6H_5)_2$, | $As(Br)(C_6H_5)_2$, | 1,10-phenantholine, |
| 2,2' dipyridyl, etc. | | |

Suitable ligands having Group VI donor atoms include those having the general formula:

$$B - R_b$$

where B represents the elements oxygen, sulfur, selenium, tellurium and polonium as donor atoms, R is selected from the group including alkyl, aryl, substituted aryl or alkyl groups or mixtures thereof, and $b$ has a value of 2. These ligands should also be capable of functioning as $\pi$-acceptor ligands. Examples of suitable Group VIB ligands are:

| | |
|---|---|
| $S(C_6H_5)_2$, | $Se(C_6H_5)_2$ |

Ligands which are suitable in Group VIIA are fluorine, chlorine, bromine and iodine.

Table III and IV show evidence for the suitability of the above named ligands.

Illustrative of the many ligand stabilized platinum-(II)-Group IVA metal halide complexes which can be used in the inventive hydroformylation as the catalyst system are:

| | |
|---|---|
| $PtCl_2[As(C_6H_5)_3]_2-SnCl_2$, | $PtCl_2[Sb(C_6H_5)_3]_2-SnCl_2$, |
| $PtCl[Bi(C_6H_5)_3]_2-SnCl_2$, | $PtCl_2[P(C_6H_5)_3]_2-SnCl_2$, |
| $PtCl_2[P(C_2H_5)_2(C_6H_5)]-SnCl_2$, | $PtCl_2[As(n-C_4H_9)_3]_2-SnCl_2$, |
| $PtCl_2[(C_6H_5)_2P(CH_2)_2P(C_6H_5)_2]-SnCl_2$, | $PtCl_2[(C_6H_5)_2-$ |
| $AsCH_2CH_2As(C_6H_5)_2]-SnCl_2$, | $PtCl_2(1,10$-Phenanthroline$)-SnCl_2$ |
| $PtCl_2[P(n-C_4H_9)_3]_2-SnCl_2$, | $PtCl_2[As(CH_3)_2C_6H_5]_2-SnCl_2$ |
| $PtCl_2[P(p-CH_3-C_6H_4)_3]_2-SnCl_2$, | $PtCl_2[2,2$-dipyridyl$]-SnCl_2$, |
| $PtCl_2(S(C_6H_5)_2]_2-SnCl_2$, | $PtCl_2[P(OC_6H_5)_3]_2-SnCl_2$, |
| $PtCl_2[P(Cl)(C_6H_5)_2]_2-SnCl_2$, | | as well as the corresponding stannous bromides, stannous iodides, and stannic chlorides, bromides, and iodides and germanium(II) halide complexes. Tables I-IV show evidence for the suitability of the above ligand stabilized platinum(II)-Group IVA metal halide complexes as hydroformylation catalysts.

C. TEMPERATURE REQUIRED FOR HYDROFORMYLATION

The temperature range which can be employed for hydroformylation is a variable which is dependent upon experimental factors including the olefin employed, the total pressure, the mole ratio of hydrogen and carbon monoxide used, the concentrations of reactants and catalyst, and particularly the choice of platinum catalyst among other things. Again using 1-heptene as a typical alpha-olefin and $PtCl_2P(C_6H_5)_3-SnCl_2$ as a representative catalyst, an operable temperature range is from about 25° to 125°C when superatmospheric pressures of greater than 100 psig are employed. A narrower range of 50°C to 100°C represents the preferred temperature range when the aforementioned olefin is hydroformylated at 500–1500 psig using the catalyst system described supra. Table V is evidentiary of how this narrower range is derived.

D. PRESSURES REQUIRED FOR HYDROFORMYLATION

The pressure range which can be employed for hydroformylation is a variable which is also dependent on the factors mentioned above. Using $PtCl_2[P(C_6H_5)_3]_2-SnCl_2$ as a representative catalyst, and 1-heptene as the olefin, an operable pressure range is from 100 to 3000 psig, with a mole ratio of $H_2:CO$ being 1:1, when a temperature range of from about 25° to 125°C is employed. A narrower range of from 500 to 1500 psig represents the preferred pressure range when the narrower temperature range of 50°C to 100°C is employed. Table V provides supporting data of how this narrower range is derived.

E. HYDROGEN TO CARBON MONOXIDE RATIO

The $H_2/CO$ mole ratio may be varied over a range of from 30/1 to 1/30 when suitable temperatures and total pressures are employed. A preferred narrower range is from 2/1 to ½ of hydrogen/carbon monoxide. Table VI gives data on the effect of $H_2/CO$ ratio on yields, selectivity, and reaction times.

F. REACTION TIMES REQUIRED

As previously indicated in the analogous discussion on temperatures and pressures required in the reaction, experimental variables are important in arriving at reaction times, Generally, substantial conversions (80% or higher) of the olefin to the linear paraffinic aldehydes can almost always be accomplished within 10 hours, with 2 to 4 hours representing the more usual reaction time interval.

G. RATIO OF STANNOUS HALIDE TO LIGAND STABILIZED PLATINUM(II) TYPE CATALYST

While the molar ratio of stannous chloride to the ligand stabilized platinum(II) type halide is not critical, the experimental work performed indicates that at least 1 mole of stannous chloride for each mole of platinum-(II) type chloride complex is required for reproducibility and good selectivity. Preferably a ratio of from 2 to 8 moles of stannous chloride for each mole of platinum(II) complex has been established to give the optimum amount of lenear paraffinic aldehyde at greatly increased rates of hydroformylation. This preferred ratio is based upon the hydroformylation of 1-heptene. Table VII documents this work.

H. RATIO OF LIGAND STABILIZED PLATINUM-(II) TYPE HALIDE-CATALYST COMPLEX TO OLEFIN SUBSTRATE

Experimental work indicates that a molar ratio of up to 500 moles to 1000 moles of alpha olefin per mole of platinum(II) type catalyst complex can be employed in most instances where alpha-olefins (as typified by 1-heptene) are used as the substrate. This minimal ratio of 0.001 moles of catalyst per mole of olefin is herein referred to as a "catalytic ratio" or "catalytic amount". Much lower ratios (i.e. 25 moles of olefin substrate per mole of platinum catalyst complex) are not harmful but are economically unattractive For this reason the favored mole ratio range arrived at in Table VII ranges from 100 to 500 moles of alpha-olefin per mole of platinum catalyst complex. Preferably the molar ratio ranges from 200 to 400 moles of olefin per mole of platinum(II) catalyst complex.

I. INERT SOLVENTS

The novel hydroformylation is run most conveniently in the presence of an inert diluent. A variety of solvents can be used including ketones such as acetone, methyl ethyl ketone, methyl isobutyl ketone, acetophenone, and cyclohexanone, aromatics such as benzene, toluene and xylenes, halogenated aromatics including ortho-dichlorobenzene, ethers such as tetrahydrofuran, dimethoxyethane and dioxane, halogenated paraffins including methylene chloride, paraffins such as isooctane, and other solvents such as acetonitrile. As the data of Table VIII indicate, the preferred solvents are polar ketones such as acetone, methyl ethyl ketone, diethyl ketone, methyl propyl ketone, methyl isobutyl ketone, and acetophenone.

J. OLEFINS AS SUBSTRATES

Olefins ranging in carbon content from 2 up to 30 carbon atoms can be employed as substrates for the hydroformylation reactions. Illustrative terminal ($\alpha$-) olefin substrates include 1-propene, 1-butene, 1-pentene, 1-hexene, 1-heptene, 1-octene, 1-nonene, 1-decene, 1-undecene, 1-dodecene, 1-tetradecene as well as their higher homologues such as 1-heptadecene, 1-octadecene, 1-eicosene, 1-tricosene, 1-pentacosene. Illustrative branched chain $\alpha$-olefin substrates include isobutylene, 2-methyl-1-pentene and 3-methyl-1-pentene. Illustrative internal and cyclic olefins include 2-butene, 2-pentene, 2-heptene, and cyclohexene, etc. These olefin substrates may be utilized in conjunction with one or more inert background solvents such as those mentioned above. The olefins can be in the form of single, discrete compounds or in the form of mixtures of olefins with or without large quantities of saturated hydrocarbon. In the latter case these comprise mixtures of from 2 to 30 carbon atoms. Table IX shows data for the hydroformylation of various olefins.

K. BY-PRODUCTS

As far as can be determined, without limiting the invention thereby, hydroformylation of olefins, catalyzed by the ligand-stabilized platinum(II)-Group IVA metal halide complexes, leads to the formation of only three minor classes of by-products. These are isomerized olefins, hydrogenated olefins and high boiling products, assumed to be condensation type products, which do not readily elute from our gas chromatography column.

The by-products may be separated from the linear paraffinic aldehydes by the usual chemical or physical techniques, such as distillation, solvent extraction, chromatography etc.

L. IDENTIFICATION PROCEDURES are by one of more of the following analytical procedures — gas chromatography (g.c) infrared, elemental analysis and nuclear magnetic resonance. Unless otherwise specified all percentages are by mole rather than weight or volume, and all temperatures are in centigrade rather than fahrenheit.

M. CONVERSION as defined herein represents the extent of conversion of the reacting olefin to other products. Conversion is expressed as a percentile and is calculated by dividing the amount of olefin consumed during hydroformylation by the amount of olefin originally charged and multiplying the quotient by 100.

N. YIELD as defined herein, represents the efficiency in catalyzing the desired hydroformylation reaction relative to other undesired reactions. In this instance hydroformylation to paraffinic aldehyde is the desired conversion. Yield is expressed as a percentile, and is calculated by determining the amount of paraffinic aldehyde product formed, divided by the amount of olefin charged and multiplying the quotient obtained by 100.

O. SELECTIVITY as defined herein is the efficiency in catalyzing a desired hydroformylation reaction relative to other undesired reactions. When $\alpha$-olefins are to be hydroformylated, hydroformylation to the linear paraffinic aldehyde is the desired conversion. Selectivity is expressed as a percentile, and is calculated by determining the amount of linear aldehyde product formed, divided by the total amount of aldehyde products formed and multiplying the quotient obtained by 100.

Having described the inventive process in general terms, the following examples are submitted to supply specific and illustrative embodiments.

EXAMPLE 1

HYDROFORMYLATION OF 1-HEPTENE CATALYZED BY BIS(TRIPHENYLPHOSPHINE)PLATINUM(II) CHLORIDE — STANNOUS CHLORIDE CATALYST COMPLEX AT HIGH PRESSURE, CONSTANT VOLUME

To a 350 ml glass liner of a rocking autoclave is added 58 ml of methyl isobutyl ketone and 7.9 ml (0.058 mole) of 1-heptene. The solution is deoxygenated with nitrogen and 0.325 g ($1.45 \times 10^{-3}$ mole) of $SnCl_2.2H_2O$ is added to the mixture and stirred 2–3 minutes until dissolved. Then $PtCl_2(PPh_3)_2$, 0.229g, ($2.9\times10^{-4}$ mole) is added, and the mixture stirred for a further 2–3 minutes under a nitrogen purge. The catalyst solution turns to a light yellowgreenish color, and although some of the $PtCl_2(PPh_3)_2$ initially remains undissolved, the mixture becomes completely homogeneous after a short period of warming and stirring under carbon monoxide and hydrogen. The loaded liner is then added to the autoclave and the apparatus is deoxygenated with nitrogen. Carbon monoxide, 750 psig, and hydrogen, 750 psig, are then charged to the reactor and the reactor is heated to 66°C with rocking for 3 hours, and the heat turned off.

After the apparatus is cooled* (9 hours) and vented, 62 ml of a greenish-red solution containing a small amount of dark solids is recovered. Gas chromatographic analysis reveals the following results:

| | |
|---|---|
| Conversion (Mole %) | 100 |
| Yield C$_8$ Aldehydes (Mole %) | 85 |
| Mole Ratio 1-octylaldehyde/2 methyl heptaldehyde | 9/1 |

| | |
|---|---|
| Isomerization to 2-and 3-heptene (Mole %) | 2.7 |

The missing 8.7 mole percent of 1-heptene is assumed to have formed high boiling products which do not come off the gas chromatograph under the conditions at which it was operated.

*The bulk of the apparatus requires this period of time to cool to ambient temperature.

EXAMPLE 2

HYDROFORMYLATION OF 1-HEPTENE CATALYZED BY BIS(TRIPHENYLPHOSPHINE)PLATINUM(II) CHLORIDE-STANNOUS CHLORIDE CATALYST COMPLEX AT CONSTANT PRESSURE

An appropriately sized reaction vessel, such as an autoclave, equipped with heating, cooling, agitating, pressurizing means, a side ampoule system for introducing charges under operation conditions, and a sampling valve, is charged with deoxygenated methyl isobutyl ketone (100 ml). To the agitated solvent under a nitrogen purge is added 0.561g of $SnCl_2-2H_2O(25 \times 10^{-4}$ moles). The reaction mixture is stirred to facilitate the dissolution of the stannous chloride, and 0.395g ($5 \times 10^{-4}$ moles) of previously prepared $PtCl_2(PPh_3)$* is added with additional stirring for 2-3 minutes. The addition of the ligand stabilized catalyst produces a yellow-green solution with some undissolved catalyst remaining. The reaction vessel is then sealed, deoxygenated, and the reaction mixture heated to 78°C under 500 psig $H_2/Co(1/1)$.** After the reaction mixture reaches temperature the 1-heptene, 13.7 ml (0.10 moles) is added to the reactor from the side ampoule at a total pressure of 1260 psig. The $H_2/CO$ pressure is maintained at 1260 psig throughout the course of the reaction by means of a pressure regulator and the reaction is monitored periodically via a sampling valve. All of the samples are clear yellow-green solutions. After 3 hours the reaction is terminated, cooled and vented off, leaving 98 ml of a clear light yellow-green solution with no solids present. The solution after a short time in the air turns a yellow-brown, but no solids are precipitated.

* Prepared by method of K. A. Jensen, Zeit Anorg. Chem. 229,225 (1936)
** Mass. Spec. analysis mole %: $H_2$,50.8; CO,48.9; $CH_4$,0.1; Ar,0.; $CO_2$,0.1

Gas chromatographic (g.c.) analysis revealed the following results:

| | |
|---|---|
| Conversion (Mole %) | 98 |
| Yield $C_8$ Aldehydes (Mole %) | 85 |
| Mole ratio 1-octyl aldehyde/2-methyl heptaldehyde | 10.1/1 |
| Isomerization to 2 and 3-heptenes (Mole%) | 9.5 |
| Hydrogenation to n-heptane(Mole %) | 3.5 |

EXAMPLES 3-6

HYDROFORMYLATION OF 1-HEPTENE CATALYZED BY $PtCl_2(PPh_3)_2+M_nCl_2$ - EFFECT OF GROUP IVA METAL HALIDE LIGANDS

Table I which follows, shows the data obtained when the designated catalysts are employed in the hydroformylation of 1-heptene using the procedure of Example 1. All the examples shown in Table I were carried out under the following conditions:

| | |
|---|---|
| Solvent - | methyl isobutyl ketone |
| 1-Heptene, | 0.88 mole per liter |
| 1-Heptene/$PtCl_2(PPh_3)_2$ molar ratio, | 200/1 |
| $M_nCl_n$/$PtCl_2(PPh_3)_2$ molar ratio, | 5/1 |
| $H_2$/CO = 1/1, | 1500 psig. |
| Reaction Temperature, | 66°C |
| Reaction Time, | 3 hours at temperature, plus 9 hours to cool to room temperature |

TABLE I

| EXAMPLE | $M_nCl_n$ | 1-Heptene Conversion | Total Yield Aldehydes | Selectivity 1-Aldehyde | Isomerization to 2,3-Heptenes | Reduction to n-Heptane | Missing Product |
|---|---|---|---|---|---|---|---|
| 3 | None | 0 | — | — | — | — | — |
| 4 | $SnCl_2$ | 100 | 85 | 90 | 3.6 | 2.7 | 9 |
| 5 | $GeCl_2{}^a$ | 14 | 14 | 98 | — | — | — |
| 6 | $SnCl_4$ | 100 | 50 | 84 | 6.5 | 8.5 | 35 |

$^a$GeCl$_2$ complex not completely solubilized

As the data of Table I indicate, meaningful hydroformylation of 1-heptene to octyl aldehyde is obtained under our preferred mild reaction conditions when a ligand stabilized platinum halide complex and the Group IVA metal halide exemplified by stannous chloride, stannic chloride, and germanium(II) chloride, are used together to form a catalyst. In the absence of these Group IVA metal halides such ligand stabilized platinum halide complexes are not effective hydroformylation catalysts under our preferred mild reaction conditions.

EXAMPLE 7-12

HYDROFORMYLATION OF 1-HEPTENE CATALYZED BY $PtX_2(PPh_3)_2+SnX_2$ — EFFECT OF HALOGEN, PSEUDO-HALOGEN AND STANNOUS HALIDE LIGANDS

Table II which follows, shows the data obtained when the designated catalysts are employed in the hydroformylation of 1-heptene using the procedure of Example 1. All the examples shown in Table II were carried out under the conditions described in Example 1 and Table I.

TABLE II

| EXAMPLE | PtX$_2$(PPh$_3$)$_2$+SnX$_2$ | Mole % | | | | | |
|---|---|---|---|---|---|---|---|
| | | 1-Heptene Conversion | Total Yield Aldehydes | Selectivity 1-Aldehyde | Isomerization to 2,3-Heptenes | Reduction to n-Heptane | Missing Product |
| 7 | PtCl$_2$(PPh$_3$)$_2$+SnCl$_2$ | 100 | 85 | 90 | 3.6 | 2.7 | 9 |
| 8 | PtBr$_2$(PPh$_3$)$_2$+SnBr$_2$ | 100 | 64 | 85 | 6.2 | 2.6 | 28 |
| 9 | PtI$_2$(PPh$_3$)$_2$+SnI$_2$$^a$ | <2 | 0.6 | — | — | — | — |
| 10 | Pt(CN)$_2$(PPh$_3$)$_2$ | 0 | — | — | — | — | — |
| 11 | PtCl$_2$(AsPh$_3$)$_2$+SnCl$_2$ | 100 | 46 | 75 | 10 | 9 | 35 |
| 12 | PtI$_2$(AsPh$_3$)$_2$+SnI$_2$$^a$ | 6.5 | 1.6 | 88 | — | — | 4.9 |

$^a$Catalyst not completely solubilized

As the data of Table II indicate, meaningful hydroformylation of 1-heptene to octyl aldehyde is obtained under our preferred mild reaction conditions when ligand stabilized platinum halide complexes and stannous halide metal salts are used together to form a catalyst. The effectiveness of the halides is in the direction Cl>Br>I. The pseudo-halide cyanide ligand was not effective in promoting hydroformylation by the catalyst Pt(CN)$_2$(PPh$_3$)$_2$ under our preferred mild reaction conditions.

EXAMPLES 13–19
HYDROFORMYLATION OF 1-HEPTENE
CATALYZED BY PtCl$_2$L$_2$+SnCl$_2$ — EFFECT OF LIGANDS WITH GROUPS VA, VIA, VIIA DONOR ATOMS

Table III which follows, shows the data obtained when the designated catalysts are employed in the hydroformylation of 1-heptene using the procedure of Example 1. All the examples shown in Table III were carried out under the conditions described in Example 1 and Table I.

EXAMPLES 20–26
HYDROFORMYLATION OF 1-HEPTENE CATALYZED BY PtCl$_2$(P(X)$_a$(R)$_b$)$_2$+SnCl$_2$ or PtCl$_2$[P(AR$_c$)$_a$R$_b$]-SnCl$_2$* EFFECT OF TRIVALENT PHOSPHOROUS LIGANDS

Table IV which follows shows the data obtained when the designated catalysts are employed in the hydroformylation of 1-heptene using the procedure of Example 1. All the examples shown in Table Iv were carried out under the conditions described in Example 1 and Table I.

* For definition of symbols X, R, A, a, b, c see page 7.

TABLE IV

| RUN | PtCl$_2$[P(X)$_a$(R)$_b$]$_2$ or PtCl$_2$[P(AR$_c$)$_a$R$_b$ | Mole % | | | | | |
|---|---|---|---|---|---|---|---|
| | | 1-Heptene Conversion | Total Yield Aldehydes | Selectivity 1-Aldehyde | Isomerization to 2,3-Heptenes | Reduction to n-Heptane | Missing Product |
| 20 | PtCl$_2$[P(Ph)$_3$]$_2$ | 100 | 85 | 90 | 3.6 | 2.7 | 9 |
| 21 | PtCl$_2$[Ph$_2$PCH$_2$CH$_2$PPh$_2$]$^a$ | 42 | 31 | 78 | 5.8 | 4.1 | 1 |
| 22 | PtCl$_2$[P(n—Bu)$_3$]$_2$ | 100 | 83 | 89 | 7.9 | 2.5 | 6 |
| 23 | PtCl$_2$[PPh(CH$_3$)$_2$]$_2$ | 78 | 59 | 87 | 9.7 | 6.3 | 3 |
| 24 | PtCl$_2$[P(p—CH$_3$·C$_6$H$_4$)$_3$]$_2$ | 90 | 78 | 93 | 8.9 | 1.9 | — |
| 25 | PtCl$_2$[P(OPh)$_3$]$_2$ | 100 | 45 | 73 | 19 | 16 | 20 |
| 26 | PtCl$_2$[PCl(Ph)$_2$]$_2$ | 100 | 72 | 89 | 13.6 | 5.4 | 9 |

$^a$Catalyst not completely solubilized

As the data of Table IV indicate, meaningful hydroformylation of 1-heptene to octyl aldehyde is obtained under our preferred mild reaction conditions when a variety of trivalent organo-phosphorous ligands are used to modify Pt(II) chlorine — stannous chloride catalysts. These include triaryl, trialkyl, substituted triaryl and mixed alkyl, aryl phosphines. Triaryl phosphites, such as triphenyl phosphite, are also suitable. Complexes with mixed substituted phosphines, such as

TABLE III

| EXAMPLE | PtCl$_2$L$_2$ | Mole % | | | | | |
|---|---|---|---|---|---|---|---|
| | | 1-Heptene Conversion | Total Yield Aldehydes | Selectivity 1-Aldehyde | Isomerization to 2,3-Heptenes | Reduction to n-Heptane | Missing Product |
| 13 | PtCl$_2$(PPh$_3$)$_2$ | 100 | 85 | 90 | 3.6 | 2.7 | 9 |
| 14 | PtCl$_2$(AsPh$_3$)$_2$ | 100 | 46 | 75 | 10 | 9 | 35 |
| 15 | PtCl$_2$(Ph$_2$AsCH$_2$CH$_2$AsPh$_2$)$^a$ | 100 | 60 | 81 | 7 | 27 | 10 |
| 16 | PtCl$_2$(SbPh$_3$)$_2$ | 94 | 61 | 75 | 12 | 8 | 13 |
| 17 | PtCl$_2$(O-Phenanthroline)$^a$ | 96 | 56 | 71 | 15 | 8 | 17 |
| 18 | PtCl$_2$(SPh$_2$)$_2$ | 91 | 52 | 72 | 9 | 8.0 | 22 |
| 19 | PtCl$_4$K$_2$ | 99 | 60 | 73 | 13 | 10 | 16 |

$^a$Catalyst not completely solubilized

As the data of Table III indicate, meaningful hydroformylation of 1-heptene to octyl aldehyde is obtained under our preferred mild reaction conditions when a variety of ligands containing Group VA, VIA and VIIA donor atoms are used to stabilize the platinum halide complexes together with the stannous halide metal salts to form a catalyst. The preferred ligands appear to be those containing a trivalent phosphorus donor atom.

PCl(Ph)$_2$, are active, as are complexes with bidentate phosphines such as Ph$_2$PCH$_2$CH$_2$PPh$_2$.

EXAMPLES 27–35
HYDROFORMYLATION STUDIES ON PtCl$_2$(PPh$_3$)$_2$-SnCl$_2$ — EFFECT OF PRESSURE AND TEMPERATURE

Table V which follows, shows the data obtained when the above designated catalyst is employed in the hydroformylation of 1-heptene using either procedure 1 or 2 of Examples 1 and 2. All of the runs in Table V were carried out under the following conditions:

| Solvent, | methyl isobutyl ketone |
|---|---|
| 1-Heptene, | 0.88 mole per liter |
| 1-Heptene/Platinum molar ratio, | 200/1 |
| $SnCl_2/PtCl_2(PPh_3)_2$ Molar ratio, | 5/1 |
| $H_2/CO$ = 1/1 | |

TABLE V

| | | | | | | Mole % | | | |
|---|---|---|---|---|---|---|---|---|---|
| Ex-<br>AMPLE | Pro-<br>cedure | Pressure<br>psig. | Temp.<br>°C. | Rx.<br>Time<br>hrs. | 1-Heptene<br>Conversion | Total<br>Yield<br>Aldehydes | Selectivity<br>1-Aldehyde | Isomerization<br>to 2,3-Hep-<br>tenes | Reduction<br>to n-Heptane | Missing<br>Product |
| 27 | 2 | 100 | 78 | (3–5) | (100) | 25 | 95 | 70 | 5 | 0 |
| 28 | 2 | 500 | 125 | 0.5 | (100) | (18) | (92) | (75) | (7) | 0 |
| 29 | 2 | 1000 | 66 | 8 | 100 | 90 | 91 | 7.3 | 2.7 | 0 |
| 30 | 2 | 1260 | 78 | 3 | 98 | 85 | 91 | 9.2 | 3.3 | 0 |
| 31 | 1 | 1500 | 24 | 20 | 58 | 57 | 91 | 1.1 | 0.3 | 0 |
| 32 | 1 | 1500 | 66 | 3 | 100 | 85 | 90 | 3.6 | 2.7 | 9 |
| 33 | 1 | 1500 | 93 | 3 | 100 | 66 | 77 | 5.6 | 3.2 | 25 |
| 34 | 1 | 3000 | 47 | 3 | 53 | 49 | 91 | 2.7 | 1.3 | 0 |
| 35 | 1 | 3000 | 66 | 3 | 100 | 88 | 89 | 5.0 | 3.8 | 3 |

As the data of Table V indicate, meaningful hydroformylation to the 1-octaldehyde is obtained between 25°C and 125°C at pressures ranging from 100 psig and 3000 psig. The preferred temperature and pressure ranges giving the best balance of aldehyde yield and selectivity to the 1-aldehyde appears to be at 50° to 100°C and 500 psig to 1500 psig.

EXAMPLES 36–40

HYDROFORMYLATION STUDIES ON $PtCl_2(PPh_3)_2$-$SnCl_2$ EFFECT OF $H_2/CO$ RATIO

Table VI which follows, shows the data obtained when the above designated catalyst is employed in the hydroformylation of 1-heptene using the procedure of Example 2. All of the runs in Table VI were carried out under the following conditions:

| Solvent, | methyl isobutyl ketone |
|---|---|
| 1-Heptene, | 0.88 mole per liter |
| 1-Heptene/Platinum molar ratio, | 200/1 |
| $SnCl_2/PtCl_2(PPh_3)_2$ molar ratio, | 5/1 |
| Reaction Temperature | 78°C |
| Total $H_2/CO$ pressure, | 1260 psig. |

TABLE VI

| | | | | Mole % | | | |
|---|---|---|---|---|---|---|---|
| EXAMPLE | $H_2/CO$ | Rx. Time hrs. | 1-Heptene Conversion | Total Yield Aldehyde | Selectivity 1-Aldehyde | Isomerization to 2- and 3-Heptenes | Reduction to n-Heptane |
| 36 | 30/1 | 1 | 100 | 56 | 93 | 26 | 18 |
| 37 | 2/1 | 2 | 98 | 81 | 91 | 12 | 5 |
| 38 | 1/1 | 3 | 98 | 85 | 91 | 9.5 | 3.5 |
| 39 | 1/2 | 4 | 98 | 83 | 92 | 12 | 3 |
| 40 | 1/5 | 10 | 100 | 78 | 93 | 18 | 2 |

As the data of Table VI show, hydroformylation may be carried out over a wide range of hydrogen to carbon monoxide ratios. The yield of aldehydes tends toward a maximum value at an $H_2/CO$ ratio of 1/1. When $H_2/CO$ ratios widely divergent from 1/1 are used reduction and/or isomerization of olefins becomes more important. Selectivity to straight chain aldehyde remains essentially constant, 92 ± 1 percent, over a wide range of $H_2/CO$ ratios. However, high ratios of $H_2/CO$ favor the rate of the hydroformylation reaction.

EXAMPLES 41–44

HYDROFORMYLATION STUDIES ON $PtCl_2(PPh_3)_2$-$SnCl_2$ EFFECT OF OLEFIN AND CATALYST CONCENTRATIONS AND $SnCl_2/PtCl_2(PPh_3)_2$ MOLAR RATIO

Table VII which follows, shows the data obtained when the above designated catalyst is employed in the hydroformylation of 1-heptene and propylene using the procedure of Example 2. All of the runs in Table VII were carried out under the following conditions:

| Solvent, | methyl isobutyl ketone |
|---|---|
| Reaction Temperature | 78°C |
| $H_2/CO$=1/1, | 1260 psig |

TABLE VII

| | | | | | Mole % | | |
|---|---|---|---|---|---|---|---|
| EXAMPLE | α-Olefin (M) | $PtCl_2(PPh_3)_2$ (M) | $SnCl_2/$ $PtCl_2(PPh_3)_2$ | Time (hrs.) | α-Olefin Conversion | Total Aldehyde Yield | Selectivity 1-Aldehyde |
| 41 | 1-Heptene 0.88 | $4.4 \times 10^{-3}$ | 5/1 | 3 | 98 | 85 | 91 |
| 42 | " 1.76 | $4.4 \times 10^{-3}$ | 5/1 | 3 | 98 | 84 | 93 |
| 43 | " 0.88 | $4.4 \times 10^{-3}$ | 1/1 | 8 | 99 | 88 | 93 |
| 44 | " 0.88 | $1.1 \times 10^{-3}$ | 10/1 | 20 | 90 | 73 | 93 |
| 45 | Propylene 1.75 | $2.2 \times 10^{-3}$ | 5/1 | 31 | >95 | 96 | 91 |
| 46 | " 1.75 | $17.6 \times 10^{-3}$ | 5/1 | 1 | >95 | 90 | 82 |

TABLE VII-continued

| EXAMPLE | α-Olefin (M) | $PtCl_2(PPh_3)_2$ (M) | $SnCl_2/PtCl_2(PPh_3)_2$ | Time (hrs.) | Mole % α-Olefin Conversion | Total Aldehyde Yield | Selectivity 1-Aldehyde |
|---|---|---|---|---|---|---|---|
| 47 | " | 2.5 | $4.4 \times 10^{-3}$ | 5/1 | 6 | >95 | 91 | 84 |

As the data of Table VII indicate, meaningful hydroformylation of olefins may be obtained at very high olefin to platinum ratios approaching 1000/1. However, the rates of aldehyde formation decrease somewhat with ratios of above 500/1. The stannous chloride to $PtCl_2(PPh_3)_2$ ratio should be greater than 1/1 to assure rapid reaction rates. A ratio of 5/1 is suitable. Selectivity to straight chain aldehyde remains essentially constant as concentrations of olefin and catalyst are varied over the ranges shown in Table VII.

EXAMPLES 48–59

HYDROFORMYLATION OF 1-ALKENES CATALYZED BY LIGAND STABILIZED PLATINUM(II) CHLORIDE-STANNOUS CHLORIDE COMPLEXES — EFFECT OF SOLVENT

Table VIII which follows, shows the data obtained when a variety of 1-alkenes are hydroformylated in the designated solvents. The hydroformylations were carried out using the procedures of Examples 1 and 2. The experimental reaction parameters are indicated. All runs were carried out at a stannous chloride to platinum mole ratio of 5.

to effect hydroformylation. In highly polar solvents like dimethylformamide and acetonitrile the catalyst dissolves readily, but the hydroformylation reaction is more or less inhibited. It may be, without limiting the invention thereby, that such solvents complex too strongly with the catalyst, and prevent coordination and/or activation of other substrates.

The preferred solvents appear to be ketones of intermediate polarity such as acetone, methyl isobutyl ketone, acetophenone, etc.

EXAMPLES 60–66

HYDROFORMYLATION OF OLEFINS CATALYZED BY $PtCl_2(PPh_3)_2+SnCl_2$ — EFFECT OF OLEFIN STRUCTURE

Table IX which follows, shows the data obtained when the designated olefins are hydroformylated using the procedures of Examples 1 and 2. All the examples shown in Table IX were carried out under the following conditions:

| | |
|---|---|
| Solvent, | methyl isobutyl ketone |
| Olefin, | 0.88 moles per liter |
| Olefin/Platinum molar ratio, | 200/1 |

TABLE VIII

| Ex. | Solvent | Platinum Complex (M) | Olefin (M) | Press. psig | Temp. °C. | Rx. Time Hrs. | Olefin Conversion | Total Yield Aldehyde | Selectivity 1-Aldehyde | Isomerization to Internal Olefins | Reduction to Alkane | Missing Product |
|---|---|---|---|---|---|---|---|---|---|---|---|---|
| 48 | Methyl isobutyl ketone | $PtCl_2(PPh_3)_2$ 0.0044 | 1-Heptene 0.88 | 1500 | 66 | 3 | 100 | 85 | 90 | 3.6 | 2.7 | 9 |
| 49 | Acetone | " | 1-Nonene 0.88 | 1500 | 66 | 3 | 100 | 87 | 92 | 9.7 | 1.3 | 2 |
| 50 | Acetophenone | " | 1-Heptene 0.88 | 1260 | 78 | 2 | 100 | 85 | 93 | 12.5 | 2.5 | 0 |
| 51 | Cyclohexanone | " | Propylene 1.75 | 1260 | 78 | 5 | ND* | 52 | 87 | — | ND* | ND* |
| 52 | Acetonitrile | " | 1-Nonene 0.88 | 1500 | 66 | 3 | 16 | 16 | 89 | 0 | 0 | 0 |
| 53 | Tetrahydrofuran | " | 1-Nonene 0.88 | 1500 | 66 | 3 | 1.6 | 1.6 | (100) | 0 | 0 | 0 |
| 54 | Dimethylformamide | " | Propylene 1.8 | 1260 | 78 | 2 | 0 | 0 | 0 | 0 | 0 | 0 |
| 55 | o-Dichlorobenzene | $PtCl_2(AsPh_3)_2$ 0.0044 | 1-Heptene 0.88 | 1500 | 66 | 3 | 100 | 57 | 67 | 7 | 19 | 17 |
| 56 | Methylene | " | 1-Heptene | 200 | 108 | 0.5 | 93 | 5 | 84 | 83 | 5 | 0 |
| 57 | Toluene | $PtCl_2(AsPh_3)_2$ 0.0019 | 1-Heptene 0.38 | 200 | 94 | 3 | 92 | 16 | 92 | 61 | 10 | 5 |
| 58 | Isooctane | $PtCl_2(PPh_3)_2$ 0.0044 | 1-Nonene 0.88 | 1500 | 66 | 3 | 5 | 5 | (100) | — | — | — |
| 59 | Isooctane | " | 1-Nonene 0.88 | 1500 | 125 | 6 | 100 | 36 | 87 | 18 | 11 | 35 |

*ND means NOT DETERMINED

As the data of Table VIII indicate, ligand-stabilized platinum(II) chloride-stannous chloride complexes catalyze the hydroformylation of olefins in a variety of highly polar, polar and non-polar solvents. In non-polar solvents such as toluene and isooctane, the catalyst is difficulty soluble, and higher temperatures are required

| | |
|---|---|
| $SnCl_2/PtCl_2(PPh_3)_2$ molar ratio, | 5/1 |
| $H_2/CO = 1/1$, | 1500 psig or 1260 psig |
| Reaction Temperature, | 66°C |
| Reaction Time, | 3–6 hours (exclusive of "cool down" periods) |

TABLE IX

| EXAMPLE | Olefin | Pressure psig | Rx. Time (hrs.) | Olefin Conversion | Total Yield Aldehydes | Selectivity 1-Aldehyde | Isomerization to 2,3-Olefins | Reduction to Alkane | Missing Product |
|---|---|---|---|---|---|---|---|---|---|
| 60 | Propylene | 1260 | 6 | 95 | 90 | 87 | — | — | 5 |
| 61 | 1-Heptene | 1500 | 3 | 100 | 85 | 90 | 3.6 | 2.7 | 9 |
| 62 | 1-Undecene | 1260 | 5 | 100 | 86 | 96 | 10.8 | 3.2 | 0 |
| 63 | 1-Eicosene | 1500 | 3 | 100 | 57 | 89 | 12.3 | 6.5 | 25 |
| 64 | 2-Methyl-1-Pentene | 1500 | 3 | 27 | 18 | 100 | 0 | 0 | 9 |
| 65 | 2-Heptene | 1500 | 3 | 6.5 | 6.5 | 3 | 0 | 0 | 0 |
| 66 | Cyclohexene | 1260[a] | 14 | 26 | 25 | — | — | 0 | 1 |

[a] Run at 108°C.

The data in Table IX demonstrate that straight chain α-olefins are readily hydroformylated. Branched chain α-olefins are less easily hydroformylated, internal and cyclic olefins are the most difficult to hydroformylate using the catalysts of this invention under mild reaction conditions.

As the numerous examples of this invention indicate, the subject invention is advantageous in several respects compared to corresponding hydroformylation of the prior art. For example, using various platinum(II) ligand stabilized-stannous chloride catalyst complexes, 1-alkenes and to some extent internal alkenes and cycloalkenes, can be hydroformylated to aldehydes at relatively mild reaction conditions of temperature and pressure. Further, for 1-alkenes, selectivities to the 1-aldehydes are generally excellent, and competing isomerization and reduction reactions are kept to a minimum. In addition favorable (large) ratios of alkene to catalyst may be employed and generally most polar solvents are suitable as reaction media.

Finally, the invention is quite advantageous in that numerous substitutions, modifications and changes can be made without departing from the inventive concept. For instance, numerous ligands such as phosphorus, arsenic and the like can be employed with various organic radicals such as triphenylarsine, triphenylphosphine and platinum(II) salts to form in conjunction with stannous chloride a highly active hydroformylation catalyst. However, the scope of the subject invention can best be understood by examining the claims which follow, in conjunction with the preceding specification.

What is claimed is:

1. A process for preparing primarily linear aldehyde products by the hydroformylation of alpha olefins containing from 2 to 30 carbon atoms, through the catalytic addition of hydrogen and carbon monoxide to said olefins at elevated temperatures and pressures consisting essentially of:
    a. admixing each mole of said alpha olefin to be hydroformylated with from 0.001 to 0.1 millimoles of a ligand stabilized platinum dihalide complex selected from the group consisting of:
    $PtCl_2[Ph_2PCH_2CH_2PPh_2]$
    $PtCl_2[P(n-Bu)_3]_2$
    $PtCl_2[PPh(CH_3)_2]_2$
    $PtCl_2[P(p-CH_3-C_6H_4)_3]_2$
    $PtCl_2[P(OPh)_3]_2$
    $PtCl_2[PCl(Ph)_2]_2$
    $PtCl_2(PPh_3)_2$
    $PtCl_2(AsPh_3)_2$
    $PtCl_2(Ph_2AsCH_2CH_2AsPh_2)$
    $PtCl_2(SbPh_3)_2$
    $PtCl_2(o\text{-Phenanthroline})$
    $PtCl_2(SPh_2)_2$
    $PtBr_2(PPh_3)_2$ and
    $PtCl_2(PPh_3)_2$
    catalyst complex, and from 0.001 to 1.0 moles of a Group IVA metal halide selected from the group consisting of $SnCl_4$, $SnCl_2$ and $GeCl_2$, said mole ratio of Group IVA halide ligand stabilized platinum II dihalide complex ranging from 1:1 to 10:1, in a deoxygenating atmosphere to form a deoxygenated reaction admixture,
    b. pressurizing said reaction admixture between about 100 and 3000 psig with an excess of carbon monoxide and hydrogen over what is required by stoichiometry to satisfy the needs of aldehyde-forming hydroformylation reaction, said mole ratio of $H_2$:CO ranging from 0.033 to 30 moles of hydrogen for each mole of carbon monoxide,
    c. heating said pressurized reaction admixture between 25°C to 125°C, until formation of said aldehyde products takes place, and
    d. isolating said aldehyde product contained therein.

2. The process of claim 1 wherein the olefin to be hydroformylated is propylene.

3. The process of claim 1 wherein the olefin to be hydroformylated is 1-heptene.

4. The process of claim 1 wherein the olefin to be hydroformylated is 1-eicosene.

5. The process of claim 1 wherein the olefina are in the form of single, discrete alpha-olefins in the admixture.

6. The process of claim 1 wherein the olefins are in the form of mixtures of alpha-olefins in the admixture.

7. A process for preparing primarily linear aldehyde products by the hydroformylation of alpha olefins containing from 2 to 30 carbon atoms, through the catalytic addition of hydrogen and carbon monoxide to said olefins at elevated temperatures and pressures consisting essentially of:
    a. admixing each mole of said alpha olefin to be hydroformylated with from 0.002 to 0.01 millimoles of a ligand stabilized platinum dihalide catalyst complex selected from the group consisting of:
    $PtCl_2(PPh_3)_2+SnCl_2$
    $PtCl_2(AsPh_3)_2+SnCl_2$
    $PtCl_2[Ph_2PCH_2CH_2PPh_2]+SnCl_2$
    $PtCl_2[P(n-Bu)_3]_2+SnCl_2$
    $PtCl_2[PPh(CH_3)_2]_2+SnCl_2$
    $PtCl_2[P(p-CH_3-C_6H_4)_3]_2+SnCl_2$
    $PtCl_2[P(OPh)_2]_2+SnCl_2$
    $PtCl_2[PCl(Ph)_2]_2+SnCl_2$
    $PtCl_2(Ph_2AsCH_2CH_2AsPh_2)+SnCl_2$
    $PtCl_2(SbPh_3)_2+SnCl_2$
    $PtCl_2(o\text{-Phenanthroline})+SnCl_2$
    $PtCl_2(SPh_2)_2+SnCl_2$ $PtBr_2(PPh_3)_2+SnBr_2$
$PtCl_2(P(Ph_3)_2+GeCl_2$, and
$PtCl_2(PPh_3)_2+SnCl_4$
catalyst complex, in the presence of sufficient inert solvent to disperse the components fo the admixture, in a deoxygenating atmosphere to form a deoxygenated reaction admixture,
b. pressurizing said reaction admixture between about 500 and 1500 psig with an excess of carbon monoxide and hydrogen over what is required by stoichiometry to satisfy the needs of the aldehyde-forming hydroformylation reaction, said mole ratio of $H_2:CO$ ranging from 0.5 to 2.0 moles of hydrogen for each mole of carbon monoxide,
c. heating said pressurized reaction admixture between 25°C to 125°C, until formation of said aldehyde products takes place, and
d. isolating said aldehyde product contained therein.

8. The process of claim 7 wherein the inert solvent is selected from the group of polar solvents consisting of acetone, methyl ethyl ketone methyl isopropyl ketone, methyl-n-propyl ketone, methyl isobutyl ketone, acetophenone, cyclohexanone, acetonitrile and o-dichlorobenzene.

9. The process of claim 7 wherein the inert solvent is selected from the group of non-polar solvents consisting of toluene, benzene and isooctane, and the temperature is maintained from 90° to 150°C at superatmospheric pressures from 100 to 3,000 psig.

10. A process for preparing primarily linear aldehyde products by the hydroformylation of alpha olefins containing from 2 to 30 carbon atoms, through the catalytic addition of hydrogen and carbon monoxide to said olefins at elevated temperatures and pressures consisting essentially of:
   a. admixing each mole of said olefin to be hydroformylated with from 0.002 to 0.01 millimoles of $PtCl_2(PPh_3)+SnCl_2$ catalyst complex, in the presence of sufficient inert solvent to disperse the components of the admixture, in a deoxygenating atmosphere to form a deoxygenated reaction admixture,
   b. pressurizing said reaction admixture between 500 and 1500 psig with an excess of carbon monoxide and hydrogen over what is required by stoichiometry to satisfy the needs of the aldehyde-forming hydroformylation reaction, said mole ratio of $H_2:CO$ ranging from 0.5 to 2.0 moles of hydrogen for each mole of carbon monoxide,
   c. heating said pressurized reaction admixture between 25°C to 125°C, until formation of said aldehyde products takes place, and
   d. isolating said aldehyde product contained therein.

11. A process for preparing primarily linear aldehyde products by the hydroformylation of alpha olefins containing from 2 to 30 carbon atoms, through the catalytic addition of hydrogen and carbon monoxide to said olefins at elevated temperatures and pressures consisting essentially of:
   a. admixing each mole of said olefin to be hydroformylated with from 0.002 to 0.01 millimoles of a catalyst selected from $PtBr_2(PPh_3)_3+SnBr_2$, $PtCl_2(PPh_3)+SnCl_2$ and $PtCl_2(PPh_3)_2+SnCl_4$ catalyst complex, in the presence of sufficient inert solvent to disperse the components of the admixture, in a deoxygenating atmosphere to form a deoxygenated reaction admixture,
   b. pressurizing said reaction admixture between 500 and 1500 psig with an excess of carbon monoxide and hydrogen over what is required by stoichiometry to satisfy the needs of the aldehyde-forming hydroformylation reaction, said mole ratio of $H_2:CO$ ranging from 0.5 to 2.0 moles of hydrogen for each mole of carbon monoxide,
   c. heating said pressurized reaction admixture between 25°C to 125°C, until formation of said aldehyde products takes place, and
   d. isolating said aldehyde product contained therein.

* * * * *